(12) United States Patent
Gildenberg (10) Patent No.: US 8,036,448 B2
(45) Date of Patent: Oct. 11, 2011

(54) METHODS AND DEVICES FOR TATTOO APPLICATION AND REMOVAL

(75) Inventor: Philip L. Gildenberg, Houston, TX (US)

(73) Assignee: Restoration Robotics, Inc., Mountain View, CA (US)

( * ) Notice: Subject to any disclaimer, the term of this patent is extended or adjusted under 35 U.S.C. 154(b) by 956 days.

(21) Appl. No.: 11/965,631

(22) Filed: Dec. 27, 2007

(65) Prior Publication Data

US 2008/0247637 A1  Oct. 9, 2008

Related U.S. Application Data

(60) Provisional application No. 60/921,875, filed on Apr. 5, 2007.

(51) Int. Cl.
*G06K 9/00* (2006.01)

(52) U.S. Cl. .......................... 382/153; 382/100; 382/162

(58) Field of Classification Search .................. 382/100, 382/153, 162; 606/9, 133, 33, 587, 187, 606/32; 428/40.1, 42.1, 195.1, 914, 202, 428/354, 41.7, 79, 348, 905, 913, 41.8; 600/587, 600/407, 306, 300; 156/230, 267, 277, 247; 378/65, 51, 64
See application file for complete search history.

(56) References Cited

U.S. PATENT DOCUMENTS

| | | | |
|---|---|---|---|
| 4,807,163 A | 2/1989 | Gibbons | |
| 5,540,657 A | 7/1996 | Kurjan et al. | |
| 5,562,613 A | 10/1996 | Kaldany | |
| 5,827,217 A | 10/1998 | Silver et al. | |
| 5,865,744 A | 2/1999 | Lemelson | |
| 5,972,111 A | 10/1999 | Anderson | |
| 6,207,874 B1* | 3/2001 | Felton et al. | 602/42 |
| 6,341,831 B1* | 1/2002 | Weber et al. | 347/1 |
| 6,488,636 B2 | 12/2002 | Bryan et al. | |
| 6,554,825 B1 | 4/2003 | Murray et al. | |
| 6,585,746 B2 | 7/2003 | Gildenberg | |
| 6,717,102 B2* | 4/2004 | Neev et al. | 219/121.68 |
| 6,884,427 B1 | 4/2005 | Barrows | |
| 6,973,931 B1 | 12/2005 | King | |
| 7,249,712 B2* | 7/2007 | Ingalls | 235/462.01 |
| 7,517,571 B2* | 4/2009 | Funke et al. | 428/40.1 |
| 2001/0027293 A1 | 10/2001 | Joshi | |
| 2002/0110672 A1* | 8/2002 | Muratore-Pallatino et al. | 428/195 |
| 2002/0133149 A1 | 9/2002 | Bessette | |

(Continued)

FOREIGN PATENT DOCUMENTS

DE 10249786 5/2004

(Continued)

OTHER PUBLICATIONS

PCT International Search Report and Written Opinion of the International Searching Authority for PCT/US2007/088975, Applicant Restoration Robotics, Inc., Forms PCT/ISA/210, 220 and 237, mailed Nov. 13, 2008 (19 pages).

(Continued)

*Primary Examiner* — Sheela Chawan
(74) *Attorney, Agent, or Firm* — Lena I. Vinitskaya (57) ABSTRACT

A robotic tattoo application and tattoo removal methods and systems are described. This technology involves the use of a robotic system guided by control of a graphics capable computer in order to perform various types, including artistic, recreational, cosmetic, or therapeutic tattooing, or tattoo removal.

21 Claims, 4 Drawing Sheets

U.S. PATENT DOCUMENTS

| | | |
|---|---|---|
| 2005/0137584 A1 | 6/2005 | Lemchen |
| 2005/0147652 A1 | 7/2005 | Atkins et al. |
| 2005/0154431 A1 | 7/2005 | Quistgaard et al. |
| 2007/0078466 A1 | 4/2007 | Bodduluri et al. |
| 2007/0078473 A1 | 4/2007 | Bodduluri |
| 2007/0078475 A1 | 4/2007 | Bodduluri et al. |
| 2007/0106307 A1 | 5/2007 | Bodduluri et al. |
| 2007/0264626 A1 | 11/2007 | DeBenedictis et al. |
| 2008/0033455 A1 | 2/2008 | Rassman et al. |
| 2008/0154247 A1 | 6/2008 | Dallarosa et al. |
| 2008/0167674 A1 | 7/2008 | Bodduluri et al. |
| 2008/0242990 A1 | 10/2008 | Zanelli et al. |
| 2009/0230269 A1 | 9/2009 | Dallarosa |

FOREIGN PATENT DOCUMENTS

| | | |
|---|---|---|
| WO | 9825666 | 6/1998 |
| WO | 00/09184 | 2/2000 |
| WO | 0149360 | 7/2001 |
| WO | 03068248 | 8/2003 |
| WO | 2007041267 | 4/2007 |
| WO | 2007092929 | 8/2007 |

OTHER PUBLICATIONS

Niki Passath, "Kurt, the tattoo robot", Nov. 26, 2002, Website printout <http://www.we-make-money-not-art.com/archives/2005/09/yesterday-at-th.php>, pages printed on Sep. 3, 2008 (2 pages).

PCT Invitation to pay additional fees of the International Search Authority for PCT/US2007/088975, Applicant Restoration Robotics, Inc., Form PCT/ISA/206 dated Aug. 18, 2008, and Annex to form PCT/ISA/2006 (8 pages).

Howstuffworks "How Tattoo Removal Works," web page accessed on Jan. 7, 2008, http://people.howstuffworks.com/tattoo-removal.htm/printable, (4 pages).

"Tattoo Machine," Tattoo machine—Wikipedia, web page accessed on Apr. 5, 2007, http://wikipedia.org/wiki/Tattoo_machine, (5 pages).

Howstuffworks "How Tattoos Work," Tracy V. Wilson, web page accessed on Nov. 30, 2007, http://people.howstuffworks.com/tattoo.htm, (5 pages).

Howstuffworks "How Lasers Work," Matthew Weschler, web page accessed on Dec. 12, 2007, http://science.howstuffworks.com/laser7.htm and http://science.howstuffworks.com/laser8.htm (2 pages).

About.com, "Tattoo Removal—Options and Alternatives," from Karen Hudson, Your Guide to Tattoos/Body Piercings, web page accessed on Dec. 13, 2007, http://tattoo.about.com/od/tatremoval/a/tatremoval.htm (2 pages).

Jennifer Y. Lin & David E. Fisher, "Melanocyte biology and skin pigmentation". Nature vol. 445, Feb. 22, 2007. Nature Publishing Group.

PCT International Search Report for PCT/US/2007/088971, Applicant, Restoration Robotics, Inc., Forms PCT/ISA.210, 220 and 237, dated Aug. 26, 2008 (19 Pages).

http://en.wikipedia.org/wiki/Melanocyte, "Melanocyte", entry last modified on Mar. 29, 2007, downloaded on Apr. 5, 2007. (3 pages).

* cited by examiner

METHODS AND DEVICES FOR TATTOO APPLICATION AND REMOVAL

RELATED APPLICATION DATA

The present application claims the benefit under 35 U.S.C. §119 to U.S. provisional patent application Ser. No. 60/921,875, filed Apr. 5, 2007 and entitled "Robotic Tattooing Method and Device."

FIELD OF INVENTION

This invention relates generally to tattoo application and removal, and more specifically to the robotic tattoo application and tattoo removal.

BACKGROUND

A tattoo is a design created on the skin, or sometimes other tissue, by the injection of pigment into the dermal layer, so it is visible through the surface. The most common type of tattooing device is a vibrating needle controlled by the operator as a hand-held tool that vibrates rapidly, ordinarily between 50-3,000 times per minute, to inject non-water soluble pigment in the desired pattern. If the injection is too deep, it may not be easily visible through the surface or may look blurred. If it is too superficial, it may not be held in proper position and may migrate to produce a blurred image or be gradually removed to produce a faded image as the dermis is recycled. Usually, the pattern is first outlined freehand with a stencil in dark colored ink, and then the colors are filled in. Ordinarily the tattooing needle injects a single color at a time, and repeated applications are necessary to produce a multi-colored pattern. Tattoo designs may be small and localized, or may be any size up to covering most or the entire skin surface.

In some cultures and in more primitive times, the pigment is placed on the skin and pushed in by needles or other relatively sharp objects held by hand, or pulled into the skin on thread that is passed into and out of the surface on a curved needle.

Some attempts have been made to automate placing of temporary decorations or tattoos on a body surface. For example, U.S. Pat. No. 6,341,831 to Weber et al. discloses a skin decoration apparatus and method for placing temporary multi-colored designs using Wirejet™ technology. The decoration is produced by a print head comprising Wirejet™ nozzles, which spray biocompatible inks or dyes onto the skin and last for at least several weeks. The Wirejet™ may be connected to a scanning mechanism to scan in one, two, or three directions. The decorations can be applied to contoured skin surfaces following flattening against a screen of intersecting wires, by robotic arm, or using z-axis technology. A computer stores the desired design and controls the firing of the Wirejet™ to produce the desired decoration.

Placing of permanent conventional tattoos generally involves using a needle that is controlled by the tattoo artist, it is inexact, tedious, time consuming, laborious, and consequently expensive. Similarly, despite certain advancements in a laser tattoo removal technology, conventional tattoo removal is done manually by a person, requires multiple sessions and suffers from many shortcomings.

SUMMARY

In accordance with a general aspect of the inventions disclosed herein, methods and systems are provided using a robot to perform tattooing or tattoo removal. As described herein, the provided systems and methods could be used for all kinds of tattooing, including cosmetic, therapeutic, dermatological, as well as recreational or artistic tattooing.

According to one aspect of the present invention, a robotic system for creating tattoos on a body surface is provided. The robotic system comprises a robotic arm; a tattoo tool carried by the robotic arm, the tattoo tool is adapted to be maneuverable by the robotic arm and operable to deliver a pigment for creating a tattoo image on a body surface; a processor configured to receive and process images of the body surface; a controller operatively associated with the processor and configured to maneuver the robotic arm based, at least in part, on the processed images of the body surface, wherein the tattoo tool comprises a penetrating distal end, and one or both of the processor and controller are configured to cause the penetrating distal end of the tattoo tool to puncture the body surface and to penetrate into tissue to create the tattoo image.

The robotic system may further comprise an image acquisition device, such as one or more video, digital or analog cameras. In some embodiments, the system further comprises a plurality of color reservoirs each containing a color pigment, and the tattoo tool may be selectively coupled to any of the plurality of reservoirs to control colors of the desired tattoo image. In further embodiments the robotic system of the present invention comprises a user interface that allows a system operator to input various instructions relating to many features of the desired tattoo image. A collection of the tattoo images may be associated with the processor of the robotic system of the present invention.

According to another aspect of the present invention, the method is provided for creating a tattoo image on a body surface using a robotic system. In one embodiment, the method comprises maneuvering a robotic arm to position a tattoo tool carried by the robotic arm proximate a location on a body surface where a tattoo image is intended to be created; and using a substantially automated process to cause a penetrating distal end of the tattoo tool to puncture the body surface and penetrate a desired depth in a body tissue to deliver a pigment to create the tattoo image. The method may further comprise obtaining an image of a body surface to be tattooed and registering the body surface to be tattooed with the robotic system. Registering the body surface to be tattooed with the robotic system may be accomplished by means of at least one fiducial mark. The fiducial mark may comprise any natural body landmark, such as pre-existing tattoos, birth marks, scars, moles, etc., or fiducial mark may be artificially created, for example, by inking or taping it to the relevant body surface. The fiducial mark or marks may be visualized by any appropriate image acquisition device to register the location of the fiducial mark to obtain fine control of the tip of the tool.

In some embodiments, the method may further comprise identifying a desired tattoo image. Identifying the tattoo image may be accomplished by many different means, for example, by selecting the tattoo image from a collection of images associated with or stored in the robotic system itself, or downloading a desired image from an external source (disk, internet, scanning), or creating a new desired tattoo image. The identified tattoo image may be further modified, as desired, for example, by changing size, shape, colors and other features to fit a particular location on a body surface, or simply to satisfy the taste of the user. A user interface could be used for modifying a desired image. The registration of the body surface with the robotic system may be continuously updated. For example, a portion of the tattoo image already applied may be used as a fiducial mark as placement of the tattoo image progresses.

In yet another aspect of the present invention, a method is provided for color matching at least one element of a new tattoo to a field on a body surface. In one embodiment, the method comprises obtaining an image of the body surface to be tattooed; identifying a field in the obtained image to which a color of at least one element of a new tattoo is to be matched; processing the obtained image to determine a color spectrum of the field; and color matching the at least one element of the new tattoo to one or more colors of the color spectrum of the field. The obtained image may be registered with a robotic system and the color matched new tattoo is placed on a body surface using the robotic system. The method may further comprise, for example, registering the three-dimensional localization of the fiducial mark to the robotic arm. In various embodiments, the field to which a color to be matched may be a pre-existing tattoo or any portion of it, and the new tattoo may be an extension, modification or enhancement of the pre-existing tattoo. Further, in some embodiments, the body surface may comprise a scar tissue or tissue with a deficient or abnormal color, the field may comprise a normal skin color, and color matching of the at least one element of the new tattoo to the field comprises adding one or more colors to the scar tissue or tissue with a deficient or abnormal color to simulate the normal skin color.

According to further aspect of the present invention, a system for color matching of at least one element of a new tattoo to a field on a body surface comprises an image acquisition device and an image processor configured for performing a color matching method of the present invention. In one embodiment, the image acquisition device is one or more cameras, such as any commercially available cameras. Instead of a camera, it could be a video recording device (such as a camcorder) or any other image acquisition device. Stereo imaging devices are very useful in the present invention, but other measuring devices may be employed to maintain a three-dimensional perspective of the skin surface. Similarly, while it is preferred that the image acquisition device be a digital device, it is not necessary. It could be, for example, an analog TV camera that acquires an initial image which is then digitized into a digital image for further use in the method of the present invention. The image processor may comprise any device programmed and configured to perform the color matching method according to the present invention. One non-limiting example of a suitable image processor is any type of personal computer ("PC"). Alternatively, the image processor may comprise an Application Specific Integrated Circuit (ASIC) or Field Programmable Gate Array (FPGA).

In accordance with yet another aspect of the present invention, an image processor for color matching at least one element of a new tattoo to a field on a body surface may be programmed, for example, with a software configured for receiving an image of a body surface to be tattooed, the image including a field on the body surface to which a color of at least one element of a new tattoo is to be matched; processing the image to analyze a color spectrum of the field; and color matching the at least one element of the new tattoo to one or more colors of the color spectrum of the field.

Moreover, the present invention also provides a robotic system for removing tattoos from a body surface. In one embodiment, the robotic system comprises a robotic arm; and a tattoo removal tool carried by the robotic arm, the robotic arm being maneuverable so that the tattoo removal tool may be placed proximate an existing tattoo on the body surface, the tattoo removal tool being operable using a substantially automated process to remove a tattoo image from the body surface. In some exemplary embodiments, the tattoo removal tool may comprise a laser, or a cannula configured for controlled delivery of a pigment. The robotic system for tattoo removal may further comprise a processor configured to analyze colors of the existing tattoo and colors of a skin in an area adjacent to the existing tattoo. In addition, it may include an image acquisition device configured for acquiring images of the existing tattoo and a skin in an area adjacent to the existing tattoo.

In accordance with still further aspect of the present invention, a method is provided for removing tattoos from a body surface using a robotic system. In one embodiment, the method comprises maneuvering a robotic arm to position a tattoo removal tool carried by the robotic arm proximate a location of an existing tattoo on a body surface; and operating the tattoo removal tool using a substantially automated process to remove at least a portion of the existing tattoo from the body surface. In some embodiments of the method of the present invention, removing at least a portion of the existing tattoo comprises applying a neutralizing pigment to the at least a portion of the existing tattoo to match the at least a portion of the existing tattoo with a color of a skin adjacent to the at least a portion of the existing tattoo.

Other and further objects and advantages of the invention will become apparent from the following detailed description when read in view of the accompanying figures.

BRIEF DESCRIPTION OF THE DRAWINGS

The invention is illustrated by way of example and not limitation in the figures of the accompanying drawings, in which like references indicate similar elements, and in which.

DETAILED DESCRIPTION OF THE ILLUSTRATED EMBODIMENTS

In the following Detailed Description, reference is made to the accompanying drawings, in which is shown by way of illustration specific embodiments in which the invention may be practiced. In this regard, directional terminology, such as "top," "bottom," "distal," "front," "back," etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The term "tool" as used in tattoo tool or tattoo removal tool with reference to tattoo placement and/or removal procedures refers to any number of tools or end effectors that are capable of placing (or removing) tattoos on and/or from a body surface. The following Detailed Description, therefore, is not to be taken in a limiting sense, and the scope of the present invention is defined by the appended claims.

Figure 1:
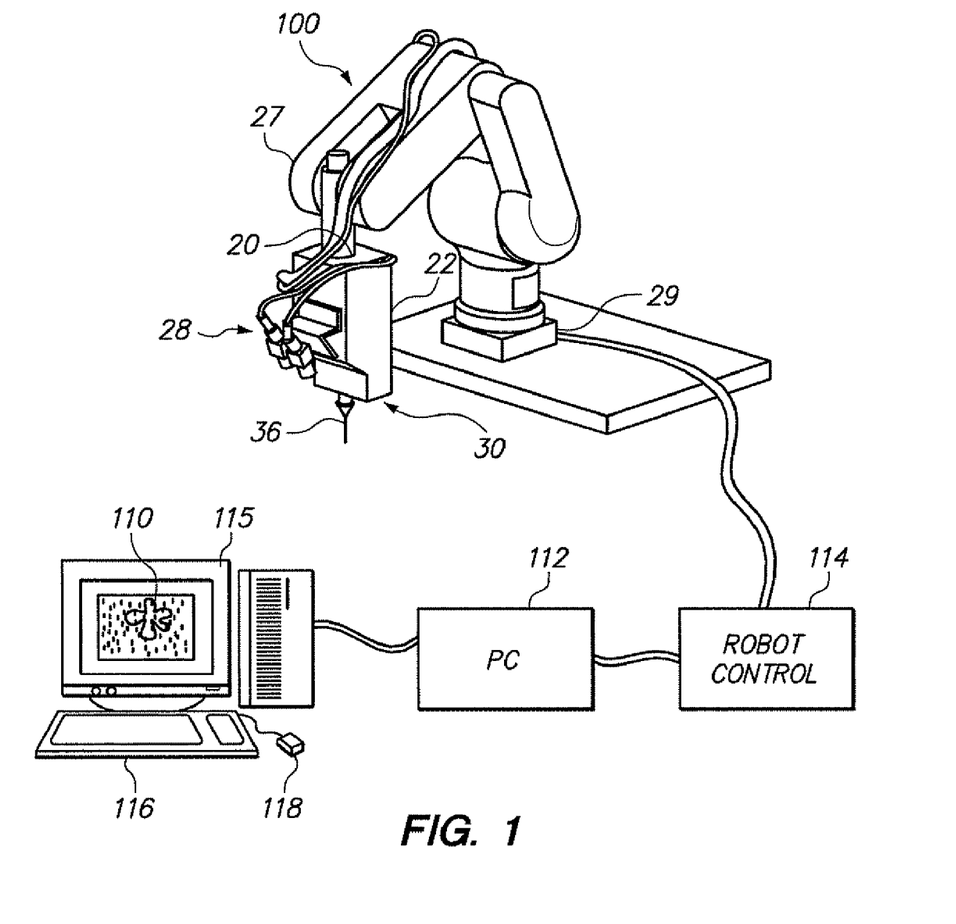
FIG. 1 is a partially schematic, perspective view of an exemplary robotic system of the present invention.

Referring now to the drawings, FIG. 1 depicts a schematic perspective view of an exemplary image-guided robotic system 100 according to one aspect of the present invention. The system 100 includes a robotic arm 27 having a tool assembly 30 that is mounted, in the illustrated embodiment, on a down tube 20 of the robotic arm 27. The robotic arm 27 may be attached to the base 29. A tool assembly 30 may include a tool housing 22 and a tattoo tool (enclosed in the tool housing 22). A cannula 36 forming a part of the tattoo tool could be seen at the bottom of the tool housing 22 in FIG. 1. However, according to another aspect of the present invention, the tool assembly 30 may instead include a tattoo removal tool that is operated by the robotic system. The system 100 also includes a processor, such as personal computer 112. The processor 112 may receive and process images acquired by an image acquisition device, such as one or more cameras 28 illustrated in this exemplary embodiment. The images may include both intradermal and subcutaneous images. The robotic system 100 of FIG. 1 may also include a controller 114 that is operatively associated with the processor (and can be a separate device or a part of the processor) and configured (alone or together with the processor) to maneuver the arm 27 in multiple degrees of freedom (for example in six degrees) based, at least in part, on images acquired by the one or more cameras 28 and processed by the processor. An operator monitors conditions and provides instructions through a monitor 115, keyboard 116, and mouse 118. The robotic system 100 preferably includes a user interface that allows a system operator to input various instructions relating to one or more of a location, orientation, depth, type, size, color, shading, or configuration of the tattoo to be placed on a body surface using the robotic system 100, or the tattoo may be designed, revised, or edited by use of the user interface. A magnified image of the body surface 110 with a tattoo image can be seen on the monitor 115.

The illustrated exemplary robotic system of FIG. 1 is useful in placing various tattoo images on a body surface, especially permanent tattoos. Tattoos can be used for artistic or recreational purposes, which are the most common forms of tattooing, in which a desired design is produced or selected from a sample collection of designs and tattooed at the desired location. Such designs may have personal significance, for instance a person's name or a motto or commercial logo (for example, "Harley-Davidson"), or may be purely decorative, for instance the picture of a butterfly or snake. Tattoos may also be cosmetic, for example, when eye or lip liner, or other facial coloring is permanently applied. Tattoos may be dermatologic or provided, for example by cosmetic surgeons, to correct a pigment defect or scarring, as in vitiligo (a skin condition where areas may be devoid of normal pigment), or used during reconstructive surgeries to correct body lines, contours and features damaged as a result of an injury.

There are numerous advantages to robotic tattooing system and method of the present invention over conventional tattooing, as described below. The robotic tattooing process itself is innately faster than conventional tattooing. Also, more precise control over location and depth of each injection could be achieved with the robotic tattooing. The computerized robotic application of the design is more precise, since conventional tattooing is free-hand and subject to errors induced by the operator, regardless of how skilled, with conceivably greater error produced by less skillful operators. Not only can the pattern be reproduced more accurately, but the depth of insertion of the pigment and the density of injection of the pigment can be precisely controlled with robotic tattooing. The depth of injection is important in defining the quality of the tattoo, and that can be precisely controlled with robotic tattooing to obtain both the ideal depth of injection of the pigment and the consistency of maintaining that depth throughout the tattooing process.

Density of pigment across each field can be more precisely controlled for a more homogeneous application of color. Because of improved precision, there can be a more precise separation of injected colors, which allows a greater color array and the use of sharply maintained color boundaries or injection of multiple colors into a single field to produce a wider variety of colors. Because the pattern is controlled more precisely, it is possible to create a more elaborate design than with conventional tattooing, with small and more precisely defined components to the pattern, which can consequently be more complex. Not only can the patterns be more artistic, but they are not limited by many of the practical considerations of tattooing or by the artistic talent of the operator.

As mentioned above in reference to FIG. 1, the tattooing robot may be programmed with a graphic interface to emulate the area of skin to be tattooed. Once the plan has been devised, the optimal plan of tattooing can be determined by the computer (for example, tattooing the outline and then filing in the fields, or tattooing each field in turn, or a to-and-fro raster pattern), the computer guides the robot to fulfill that plan. If desired, an operator may introduce manual editing at any point in the development of the tattoo specifications. Both may involve videographic registration, that is, the area of interest or part of the surface of the area is visualized, for example, by one or several video cameras that are positioned in a known relationship with the robot, so that the relevant area or surface can be registered in space to the robot to allow the tool or end effector controlled by the robot to accurately address the proper area on the body. The robotic system houses the design to be tattooed and then effectuates the tattooing or tattoo removal accurately into or from the chosen area. In one exemplary embodiment, it involves video registration to localize the subject structure in space in relation to the robot or robotic arm and registration of the desired surface to the tool carried by the robotic arm.

According to the robotic tattooing method of present invention, the subject area or body surface to be tattooed is registered to the position of the robot in space. This may require two or more degrees of registration. One or several video cameras 28, as those shown in FIG. 1, may obtain images and localize in space the surface area to be tattooed. In one embodiment, two video cameras with overlapping fields of view are provided for obtaining stereo images for fine localization of the tattoo application area. In images from the both cameras there must be a spot or spots that computer can recognize as the same spot or spots (fiducials) in order to generate three-dimensional contour of the area to be tattooed. If the relevant area on the skin does not have sufficient identifiable fiducial marks or spots, such as naturally occurring blemishes, anatomical landmarks, birth marks or other natural identifiable structures, the registration of the area to be tattooed may be facilitated by the use of videographically identifiable fiducial marks that are, for example, taped on or inked on the skin for that purpose. The field may be localized in relation to a body part, such as the ankle or arm for circumferential tattoos, the nipple, umbilicus, sacral and buttock contour, or any other visible anatomical structure. Multiple video perspective for large scale registration of a relevant body part may be used.

The site of pigment injection may be very precisely controlled by continuous feedback from an image acquisition device, such as single or stereo video cameras which could be mounted anywhere in the robotic system, for example, on the tool assembly 30, as shown in FIG. 1, or mounted near the end of the robotic arm 27, or other suitable location. This assures very precise localization of the tattoo pattern in relation to the anatomical structure or fiducials. Continual video monitoring of the part of the tattoo already applied permits continuous precise registration to the tool, which assures that the newly injected pigment aligns precisely with the part of the pattern that has been already deposited in the skin or other tissue. The portion of the tattoo that has been already applied may become a fiducial mark as procedure progresses. The provided system may further comprise a feature that allows for an ongoing comparison of the applied tattoo design to the selected one (or stored in the system) and aborts the operation or provides a signal warning if the applied design deviates from the intended chosen design. That could be accomplished, for example, with fuzzy logic comparison.

While the use of the image acquisition device comprising stereo video with two video cameras provides an advantage of registering the target skin surface as a 3-D volume, so the contour of the skin surface can be determined, embodiments of the present invention may be also used with a single camera and a range finder as known in the art. The range finder, for example, could be a laser range finder of sufficient accuracy. A single camera with a range finder can precisely measure points in space, such as the point of impact of the tattoo needle, and information is gathered as a series of points in space images. Moreover, in some embodiments, stereo cameras and a range finder combination could be used. That will allow to accurately determine the contour of the relevant skin portion, as well as the impact touch of the tattoo needle or a target for the jet injections, as further described in reference to FIG. 4. As one example, a device that actually touches the surface at or near point of injection could be provided. It could be, for example, a "finger" mounted on a transducer to provide haptic feedback in addition to video camera or cameras.

In the illustrated robotic system of FIG. 1, the controller could maneuver the robotic arm so that the arm accurately brings the tattoo tool (or tattoo removal tool according to another aspect of the present invention) to the desired point at the desired distance from the surface. In that respect, the movement of the arm (with the appropriate tool associated with the arm) could be used to place the entire desired tattoo images and designs on the body surface (or remove them). In alternative embodiments, the movement of the robotic arm that could be distorted by the mechanical inertia may not be ideal to produce very fine designs. In those embodiments, the robotic arm could provide the larger movements, for example, for automatic readjustment and repositioning as the tattooing procedure proceeds, or to draw an outline of the proposed design, or to accomplish movements larger than a certain distance (e.g. 1-2 mm). At the same time, the fine movements associated with some aspects of the tattoo design may be provided by the tattoo tool or tattoo removal tool accordingly. In one specific example, the entire tattoo design can be divided into certain segments (such as squares), and the movement of the robotic arm will allow to move the tool in turn to center it on each segment while the movement of the tool itself fills in each segment. The fine movements of the tool may simulate the movement of the tattooing needle held by an artist. Fine adjustments may be obtained by mounting the tool on a system that moves the tip of the tool in controlled three-dimensional space. One or a plurality of motors could be used to provide the "to-and-fro" and the "fore-and-aft" movements of the relevant part of the tattoo tool (or tattoo removal tool).

The use of the robotic system of the present invention provides additional advantage of easy access and broad selection of the potential tattoo patterns and designs, as the image to be tattooed is defined. Conventional tattooing involves either the use of designs that are uniquely drawn by the tattoo artist or the design is selected from a stock collection of designs and then transferred free-hand or by stencil tracing onto the surface to be tattooed. Robotic tattooing may use both of those sources for designs, that is one uniquely drawn or one from a stock collection or catalog but with substantial advantages. The uniquely designed pattern may be developed with the use of a computer design program, or the pattern may be drawn on paper and scanned into the system processor, for example, a computer. Alternatively, a digital photograph may be used or a conventional photograph scanned into the computer, so that, for instance, instead of a tattoo spelling the word "Mother", the tattoo may consist of an actual photograph of the subject's mother. The image can be of various sizes as appropriate for various body surfaces. The stock designs can be stored on a disk or any other appropriate means of storage. Alternatively, the stock catalog or collection may be housed in the computer as individual files and thumbnail displays used to select a design. Once the design for robotic tattooing is selected, the size may be computer adjusted to fit the area to be tattooed or other modifications, including modification desired by the user or the operator, could be made with use of computer graphics using methods known in the art. Computer graphics can likewise be used to modify an existing tattoo to make a more desirable design. Various modifications could be made using user interface.

Colors can be selected or modified as part of the design program. The colors can be selected by artistic criteria or can be selected by the computer, based on the colors related to the skin or other tissue area where the tattoo is being applied. Complementary colors can be used to optimize the visual perception of the design, particularly if the tattoo is being done on tissue that is pigmented, irregularly pigmented, or scarred. If abnormal pigment exists, colors can be selected to be corrective, as can the design as a whole.

Once the desired image to be tattooed is fully identified and adjusted (including adjusting size, color or any other desired feature), the robotic system may begin operating the tattoo tool to create the desired tattoo image on the body surface.

In another aspect of the present invention, method and system are provided for color matching at least an element of a new tattoo to a field or features in the relevant area of the body surface. For purposes of the present disclosure, the term "color matching" is used in its broadest sense, and is intended to include finding and producing complimentary colors, neutralizing colors, or achieving any desired color combinations, or using one color on top of another to create a third desired color, as further explained below. In one example, the new color could be matched to the color of the skin, or the existing tattoo, or any of its portion. Because the image acquisition device, such as video cameras, are part of the robotic system and are mounted to visualize the target body surface and the new tattoo as it is produced, this imaging system together with a processor may also be used to analyze the color spectrum of a field or a feature of interest, for example, a skin or its portion, or any discoloration, or any portions of a prior tattoo. The color spectrum may be analyzed, for example, with a chromatograph or similar color identification process. As a result of such analysis, any one or all elements of a new tattoo (which includes any extension or modification of the existing tattoo) can be color matched precisely, or be made complimentary.

Figure 2:
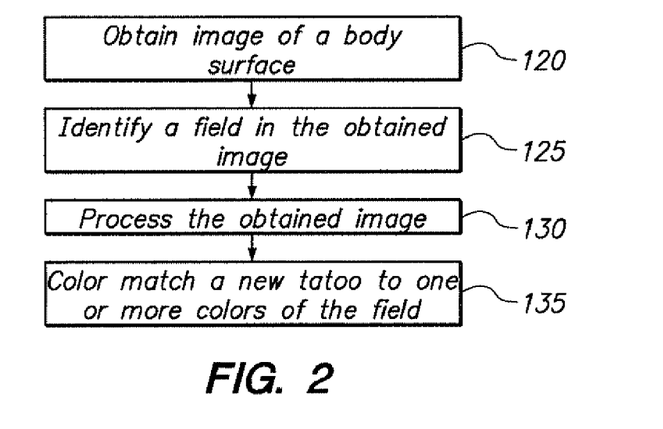
FIG. 2 is a flow diagram of one exemplary method of color matching according to the present invention.

The basic steps of the exemplary method for color matching at least one element of a new tattoo, or the whole new tattoo to a field on a body surface are summarized in a flow diagram of FIG. 2. This new tattoo could be placed next to the existing tattoo or other naturally occurring or artificial body landmark, it could be placed over the existing tattoo to modify or extend it, it could be placed next to or at least partially over the existing body mark (for example, scar tissue, disfigured tissue, or tissue with absent, deficient or abnormal pigment, birth mark, etc.) to hide it, or to highlight it, or for any other desired reason. At step 120, an image of a body surface to be tattooed is obtained. A field in the obtained image to which a color of at least one element of the new tattoo to be matched is identified at step 125. At step 130, the obtained image is processed to determine a color spectrum of the field. The processing step may involve analysis of the colors of the color spectrum of the field using, for example, one or both of the image acquisition device and the processor illustrated in the exemplary embodiment of FIG. 1. The processed image may be registered with the robotic system and the goal of the color matching may be defined (whether it is to match colors precisely, or to find colors complimentary to the normal colors of the skin or other natural marks or pre-existing tattoos on the skin, or to create the desired combination of colors). At step 135, a new tattoo or at least one element of the new tattoo is color matched to one or more colors of the color spectrum of the field. In further optional step (not shown in a flow diagram of FIG. 2) an element of the new tattoo that is color matched as explained above is placed on the body surface by the robotic system. This process could be repeated many times to place additional elements of the new tattoo, as desired.

Thus, an old tattoo can be accurately extended, can be supplemented by an accurately determined complementary color, or color can be added to pigment already in the skin from a prior tattoo to enhance it or to blend a different color. For example, blue can be added to a preexisting yellow pigment to make green; colors may be added to red scar tissue, or disfigured tissue, or tissue with absent, deficient or abnormal pigment, to simulate normal skin color.

Further, a system for color matching a new tattoo or an element(s) of a new tattoo to a field on a body surface is provided. In an exemplary embodiment, the system may comprise an image acquisition device and an image processor. Some non-limiting examples of an image acquisition device include one or more cameras, such as any commercially available cameras. The image acquisition device may take still images, or it could be a video recording device (such as a camcorder) or any other image acquisition device. Stereo imaging devices are currently preferred, but it is not necessary to have stereo imaging and the present invention is not so limited. Likewise, although it is preferred that the image acquisition device be a digital device, it is not necessary. For example, the image acquisition device could be an analog TV camera that acquires an initial image which is then processed into a digital image for further use in the embodiments of the present invention.

The image acquisition device of the color matching system, for example, one or more cameras, may be mounted in a fixed position, or it may be mounted to a robotic arm or other controllable motion device, or both. The robotic arm or motion device may be operatively coupled to a controller configured to control the motion of the robotic arm or motion device. The controller may receive and process images or data from the image processor with the controller configured to control the motion of the robotic arm or motion device based on the images or data acquired by the image acquisition device. In addition, the system may comprise other tools, devices and components useful in tattoo modifications, extensions or tattoo applications requiring color matching.

In one exemplary embodiment of the present invention, a system for color matching a new tattoo or at least one element of a new tattoo to a field on a body surface comprises an image acquisition device and an image processor, the image processor configured for processing an image obtained by the image acquisition device, the obtained image including a field to which a color of at least one element of a new tattoo to be matched; analyzing a color spectrum of the field; and color matching the at least one element of the new tattoo to one or more colors of the field.

According to the further aspect of the present invention, the image processor may comprise any suitable device programmed and configured to perform the method of color matching according to various embodiments of the present invention as described above. In one exemplary embodiment, the image processor for color matching at least one element of a new tattoo to a field on a body surface is configured for receiving an image of a body surface to be tattooed, the image including a field on the body surface to which a color of at least one element of a new tattoo is to be matched; processing the image to analyze a color spectrum of the field; and color matching the at least one element of the new tattoo to one or more colors of the field.

The image processor may be further configured to analyze and choose colors based at least in part on a certain selected criteria, for example, a specific goal that is selected by the user. By way of example, and not limitation, a suitable image processor may be any type of personal computer ("PC"). Alternatively, the image processor may comprise an Application Specific Integrated Circuit (ASIC) or Field Programmable Gate Array (FPGA).

As will be appreciated by those skilled in the art, the use of a robot for tattooing or tattoo removal provides significant advantages over the conventional manual techniques presently available for tattooing or tattoo removal. More specifically, robotic tattooing allows injecting a pigment to create tattoos using more advanced tools as described below in reference to another aspect of the present invention. Several exemplary embodiments of the tattoo tool and assembly of the present invention for use with the robotic system and method are described in reference to FIGS. 3 and 4. The following depictions are for illustration purposes only and do not necessarily reflect the actual size, shape, or dimensions of the illustrated tools. These embodiments are simply representative examples and many other modifications are within the scope of the present invention.

Commonly assigned U.S. patent application Ser. No. 11/621,087 filed on Jan. 8, 2007 discloses a robotic system including a modified conventional tattoo machine mounted on the robotic system and configured for controlled delivery of pigment ink for generating tattoos ("the '087 application"). The '087 application discloses a tool assembly shown and described herein in reference to FIG. 3.

Figure 3:
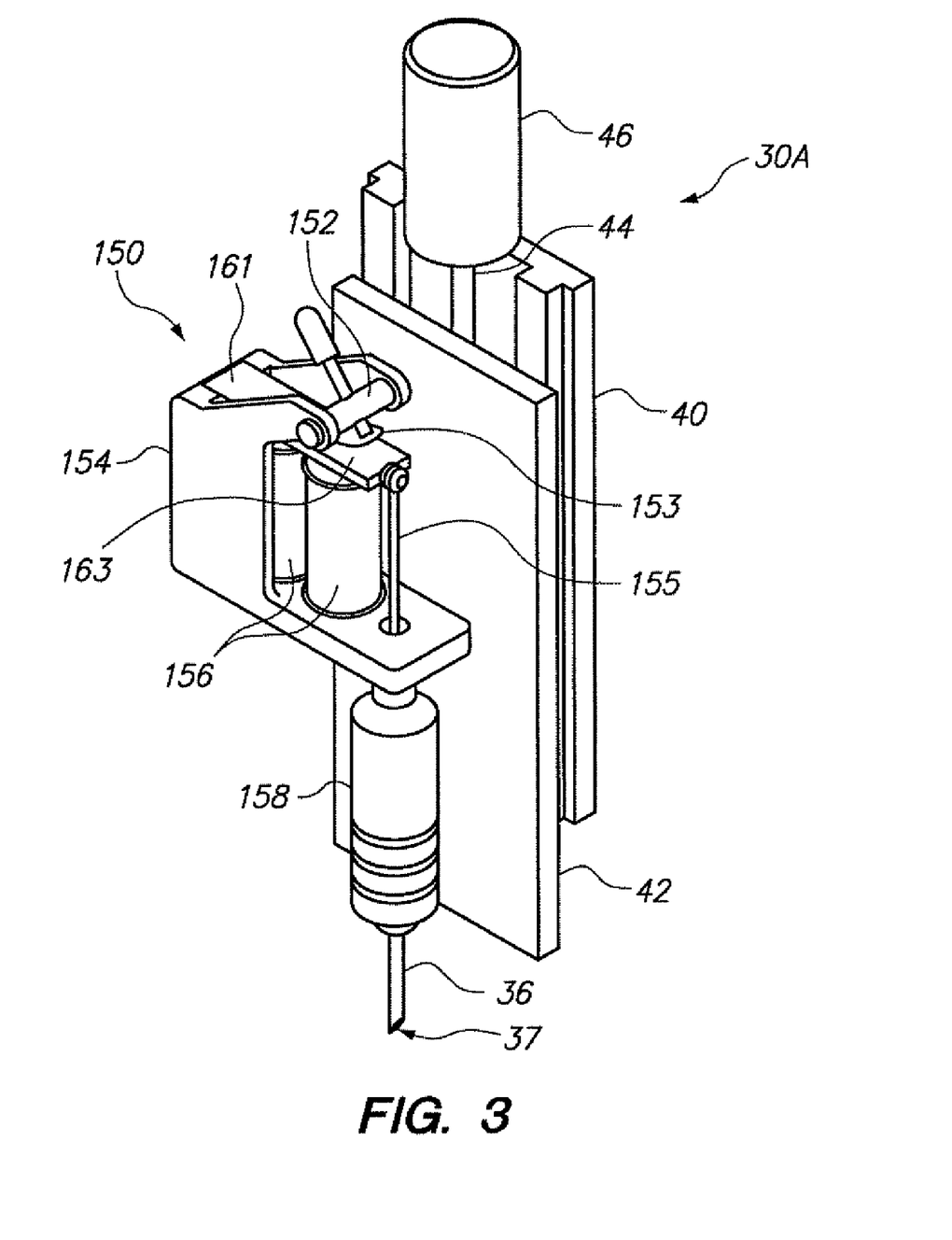
FIG. 3 is a partially schematic, perspective view of one exemplary embodiment of the tattoo tool assembly carried in the housing of the system of FIG. 1, and configured for delivery of pigment ink for generating body surface tattoos.

FIG. 3 is a partially schematic, perspective view of a tool assembly 30A, which may be mounted in the tool housing 22 of the robotic system 100 as shown in FIG. 1, and is configured for controlled delivery of pigment ink into targeted dermis tissue through the cannula 36 for generating tattoos. The tool assembly 30A may include an anchor plate 40 fixed to an inner wall of the housing 22, and a tattoo delivery tool plate 42 movably coupled to the anchor plate 40 along a screw or similar longitudinal tack 44 relative to the anchor plate 40, controlled by a motor 46. A conventional tattoo machine or tattoo tool 150 (with modifications) may be fixed to the tool plate 42. The cannula 36 comprises the tissue piercing tip 37, for example, a needle. In one exemplary embodiment, a common conventional tattooing needle could be used which consists of a vibrating needle. It could deliver a single pigment at a time from a small reservoir incorporated into the needle.

Advantageously, operation of the tattoo machine 150 could be under common control with the robotic system 100, wherein the tissue piercing or penetrating tip 37 of the cannula 36 may be positioned and oriented relative to a targeted skin surface as described above. Movement of the cannula 36 relative to the skin surface may be accomplished by relative movement of the robotic arm 27 (under image guidance), the tool plate 42, or a combination of each. Preferably, however, those actuations are made only for positioning the cannula tip 37 at the skin surface (akin to a conventional human "tattoo artist" holding a tattoo machine in position at the skin surface). Actual penetration of the skin surface and delivery of the pigment ink may be performed by the tattoo machine 150, which is under common control with the robotic system 100. A summary description follows of the main components and operation of the tattoo machine 150, with an attribution to http://en.wikipedia.org/wiki/Tattoo machine as the source of this information.

Generally, the tattoo machine 150 may employ an alternating current charge that causes electromagnets 156 to pull downward on an armature bar 163, which in turn pulls down on a reciprocating rod 155 that drives the cannula 36. The downward motion of the bar 163 also disconnects the circuit and allows an upward force of a spring ("armature spring") 161 to pull the armature bar 163 back to its initial position. More particularly, alternating current power is conducted in one direction through a pair of electromagnetic coils 156 mounted on a conductive frame 154, to an adjustable contact screw 152; and in another direction through the frame 154 to a contact spring 153, via the armature spring 161. By way of example, the frame 154 can be made of a conductive material such as iron, brass or copper and plastic bushings at the contact points are to be used to isolate the current from the frame. Alternatively, the frame may be made of a non-conductive material, with a yoke provided to connect the coils to the wiring for completing a circuit. Current flowing between the contact screw 152 and the contact spring 153, completes the circuit, thereby causing the electromagnetic coils 156 to pull down on the armature bar 163, which in turn causes the reciprocating rod 155 and (in turn) cannula 36 to move with it, such that the tissue piercing distal tip 37 of the cannula 36 may puncture and penetrate the skin surface. Once the circuit is broken, the armature spring 161 exerts an upward force, pulling the reciprocating rod with it, causing the distal tip 37 to be pulled back out of the skin surface. This motion also cause the circuit to again close with the contact made between the contact spring 153 and adjustable screw 152. The process may be repeated at a relatively fast rate, e.g., between 80 and 150 times a second. A capacitor (not shown) may be provided to regulate current flow through the tattoo machine 150. An ink reservoir 158 is coupled to the respective reciprocating rod 155 and cannula 36, and provides a source of pigmentation ink in fluid communication with the cannula 36. Injection of pigment could be done through a hollow needle through a series of very rapid injections and withdrawals. In some alternative embodiments, the needle can be connected to several ink reservoirs (not shown) so that pigment may be alternated as required for the individual pattern.

It should be appreciated that the illustrated tattoo gun 150 is provided by way of example and not limitation. Many variations and alternatives are available and will be apparent to those skilled in the art for providing a reciprocating cannula 36 for controlled delivery of the pigment (tattoo) ink, which may be advantageously positioned (and held) by the robotic arm 27 and/or movable tool plate 42, or any other form of attachment.

Figure 4:
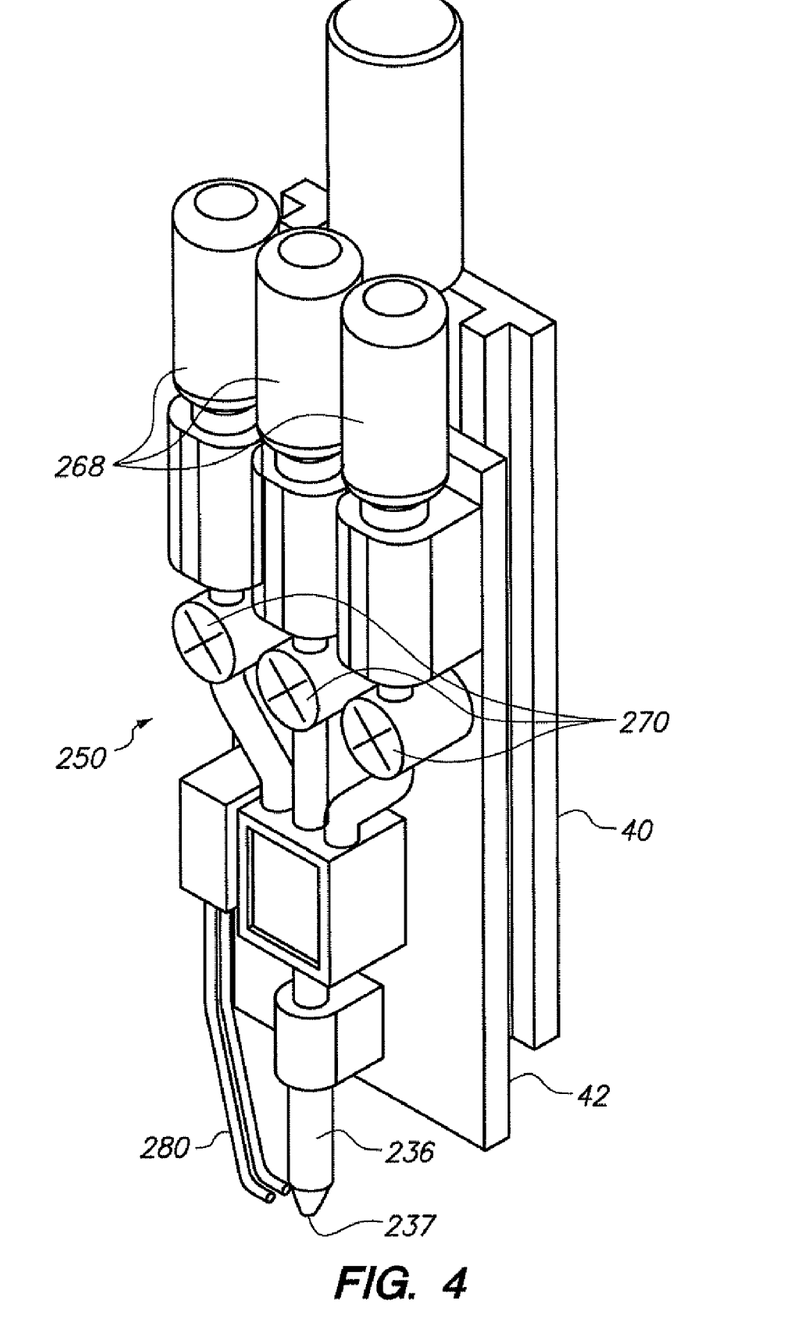
FIG. 4 is partially schematic, perspective view of another exemplary embodiment of the tattoo tool assembly according to various additional aspects of the present invention.

FIG. 4 shows another embodiment of the tattoo tool 250 and assembly of the present invention. FIG. 4 illustrates several alternative inventive concepts and features that could be combined in one embodiment as illustrated in FIG. 4, or any one of them could be used separately or in any combination in various alternative embodiments. Robotic tattooing system of the present invention may incorporate several safety features that are generally not available with the conventional manual tattoo machines. First, a disposable tattoo tool 250 can be mounted on the robotic arm to avoid cross-contamination between subjects or transmission of disease or infection. Second, one type of tattoo tool used for permanent tattoo placement, described below in reference to FIG. 4, uses pressure injection, rather than needle injection, in which only the pigment itself enters the surface of the skin. Since the tattooing industry is not regulated, such considerations may have significant impact on safety. The ability to produce the tattoo without needle injection techniques have not only safety benefit, but may make tattooing less painful.

With reference to FIG. 4, the elements similar to features of the exemplary FIG. 3 are identified with the same reference numbers. For example, as the tattoo tool of the embodiment of FIG. 4 may be attached to the robotic system in a way similar to that shown in FIG. 3, the reference numbers 40 and 42 represent the anchor plate 40 and the tool plate 42 similar to those shown in FIG. 3. Of course, as it will be understood by those skilled in the art, it is not necessary to use the anchor plate 40 and the tool plate 42 for the attachment of the tattoo tool 250, and any other appropriate forms of attachment are within the scope of the present invention. As mentioned above, the tattoo tool 250 may be removably or permanently attached and carried by the robotic arm. A pressurized injection system that does not use a needle is shown by example in FIG. 4 and represented by pressure cannula 236 having an air nozzle 237. The pressure cannula 236 of the tattoo tool 250 may be similar to that used for mass inoculations or immunizations, and it can be used to inject the pigments with a fine controlled stream, whose power can be precisely controlled, so that the pigment itself is the only thing to breach the surface of the tissue. For example, the cannula 236 designed similar to the pressure immunizations cannulas may use a brief blast of air to carry serum through the surface of the skin to the dermis, and may require an air pump, reservoir, and tubing leading to an opening that would gather all the air pressure into one fine point. The pigment or ink for tattooing could be introduced into the air stream just proximal to the opening.

Alternatively, the pressure cannula 236 can be configured according to the operating principles of a pneumatic needleless injection technique, for example, an ink jet computer printer, which would allow precise control over both the image and the color. A very small droplets of ink could be used to create a desired image (for example, 50 and 60 microns in diameter), they are positioned very precisely with a high resolutions and allow to create photo quality images. The depth of the injection could be controlled by changing the air pressure. Moreover, the computer could measure the depth by manipulating, for example, an optical spectrum that the imaging device sees.

With further reference to FIG. 4, another feature provided by embodiments of the present invention is demonstrated. The exemplary tattoo tool may be attached to a plurality of color reservoirs 268. In some embodiments, three exemplary color reservoirs could be used. Any color can be produced by the proper selection from such three reservoirs, similar to the way a myriad of colors can be applied by a computer printer with three color cartridges. Series of mini-valves 270 allow to open and close, and to provide any desired combination of colors to the tattoo tool for tattoo application. Such valves may be located on the tool assembly itself as shown, or they could be remotely attached to the tool (not shown). The tattoo tool may be operated by the robotic system to apply each color in turn, moving injection site from one to the next before changing color. Alternatively, it can alternate injection of various colors, or inject from several reservoirs simultaneously to produce the desired hue. The switching or colors is controlled with a high speed and the warnings may be provided to warn of low ink supply in any of the reservoirs.

The illustrated tool assembly provides for an additional feature that allows to clear any pigment remaining on surface as tattoo progresses as represented by the exemplary wiper 280. The computer may further calculate and indicate in advance how much of each pigment is needed, so that the tool can be appropriately loaded ahead of time.

Having more sophisticated tools leads also to improved motion of the tool. In conventional tattooing, ordinarily the outline of the pattern is first drawn, either by ink on the surface or dark pigment injected into the tissue surface. The various fields are then filled in one color at a time. This involves imprecise manual back-and-forth motion that may produce an uneven distribution of pigment or an uneven depth of pigment deposit.

Robotic tattooing with a tool that allows control of more than one pigment at a time allows a motion like a computer printer, precisely moving back and forth in a raster pattern and developing the image one row at a time. Conversely, the option exists to tattoo one color at a time, if that is indicated by the nature of the design, with the robotic arm moving, for example, from one field to another having the same color. Control over the motion of the tool also permits more precise definition of the pattern and control over depth of pigment injection.

The present invention also provides for systems and methods for robotic tattoo removal. There are many reasons why people are interested in removing unwanted old tattoos. Tattoo pigment usually resides in the deep layers of the skin which makes it difficult to remove. There are only several limited options available for such tattoo removal. Among those are various creams that are not very effective, dermabrasion procedure which is painful as it "sands" away the top layer of skin through abrasive friction, an excision procedure where the tattoo would be cut away and skin sewn back together leaving frequently an unsightly scar. These procedures generally cause much damage to the skin, scarring, they are not very effective and are largely replaced now by the use of a pulsed laser. The type of the laser is selected depending on the color of the pigment to be removed. For example, different laser wavelengths are used to target different colors of tattoo. The operator moves the laser back and forth over the appropriately colored field for a measured time. The pigment absorbs laser light more efficiently than the surrounding tissue, and consequently the pigment is affected more than the surrounding tissue. The goal is to break up the pigment, and then let the body's scavenger processes removed the smaller pigment particles over the subsequent four to six weeks. The procedure is ordinarily done in many small steps and 5 to 15 treatments are usually required, so as not to cause scarring or to overwhelm the body's ability to remove the foreign pigment bodies, and is consequently many times more expensive than tattoo application. It is ordinarily painful, since the pigment is selectively heated by the laser at a locus that houses pain nerve endings.

Robotic tattoo removal provides many advantages, as were already discussed above with reference to robotic tattoo application. Robotic tattoo removal is more efficient and consequently less expensive, less painful, and potentially more complete. Since the process is automated, it takes less time to apply the laser optimally each session with finer control than can be achieved manually, to minimize injury to adjacent tissue. The robotic procedures also allow more flexibility and effectiveness in removing tattoos completely, as well as minimizing them by tattoo modification, alteration, or touch up.

In one exemplary embodiment, the robotic system illustrated in FIG. 1 may comprise a tattoo removal tool assembly 30 carried, for example, by the robotic arm 27. One such tool or end effector carried by the robotic arm may be a laser tattoo removal tool. Some of the examples of the type of the lasers that could be used with the present invention are the Q-switched Ruby, the Q-switched Alexandrite, or the Q-switched Nd:YAG. The Q-switching technique refers to the laser's short high energy pulses. It is also useful in the present invention to use the type of laser that allows delivery of energy below the surface, such as the Nd:YAG laser. In one preferred embodiment, the localization of the laser beam(s) is based on three-dimensional targeting, rather than the two-dimensional approximate targeting of conventional procedures, where the third dimension allows the operator to designate the target at the precise depth of the pigment.

It is preferred that such laser tattoo removal tool has a narrow beam (1-2 mm) to more selectively radiate the pigment and to minimize heating of the surrounding normal tissue. However, the beam size and shape could be chosen smaller or larger depending on the size, location and colors of the tattoo to be removed or modified.

In one preferred embodiment the laser tattoo removal tool may comprise a fiberoptic laser delivery system. The image acquisition devices, such as video cameras, can monitor by infrared the heat produced and move the laser to a new area when a specific temperature is reached and then back again as needed to produce the least pain with the best treatment. Several types of laser energy can be delivered through a single tool carried by the robotic arm, and the type and proportion of each laser controlled for optimal benefit, based on video analysis of the color spectrum and the amount of the pigment being treated. Such multi-source laser treatment is more efficient, better geared to the color selection to be removed and with less laser radiation to normal skin. In some alternative embodiments, two or more lasers may be mounted on the robotic arm of the robotic system of the present invention for either consecutive or simultaneous, or any combination of the above operation by the robotic system to remove unwanted tattoos.

Figure 5:
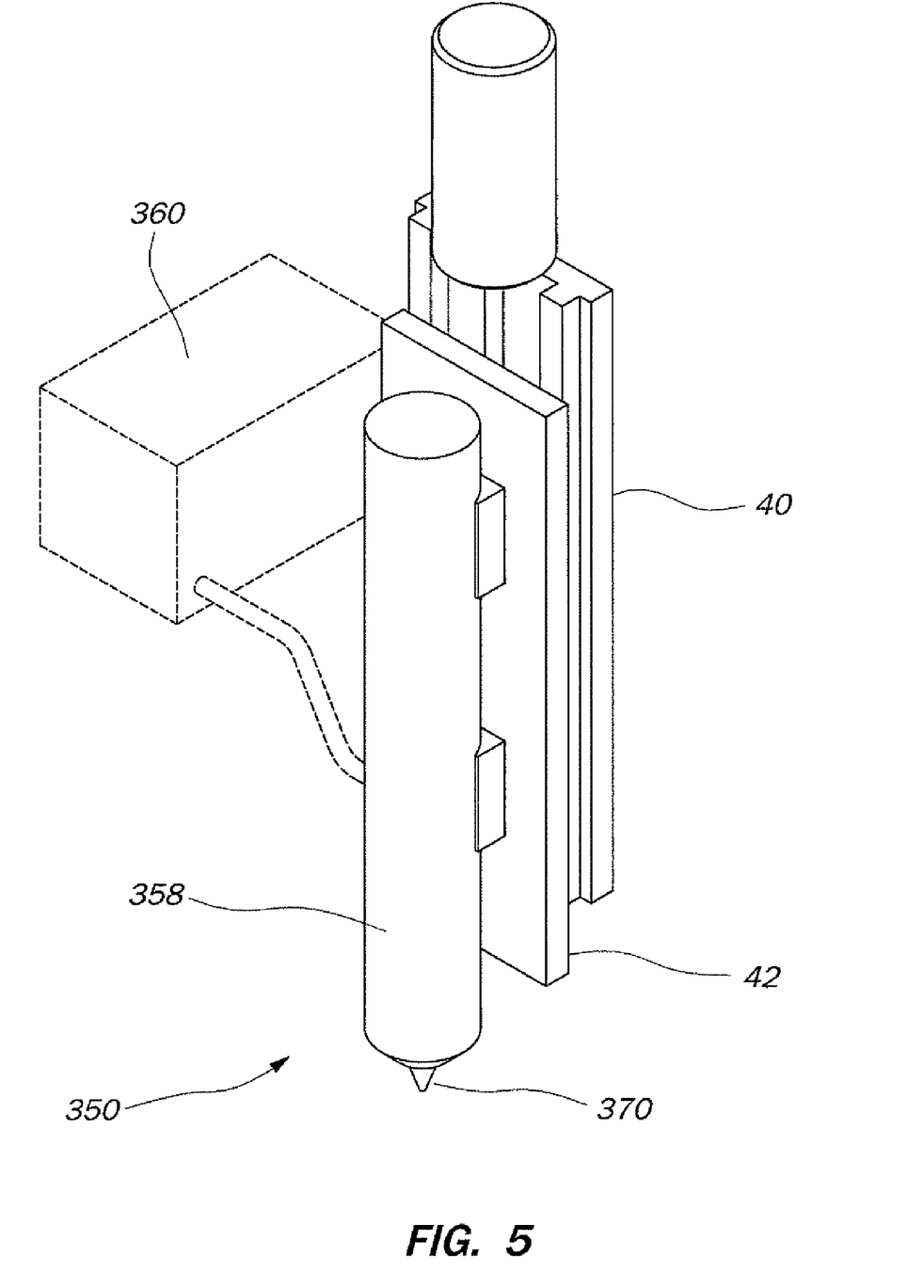
FIG. 5 is partially schematic, perspective view of one exemplary embodiment of the tattoo removal tool according to the present invention.

An exemplary embodiment of the laser tattoo removal operated by the robotic system is shown in FIG. 5. As in FIGS. 3-4, reference numbers 40 and 42 refer to the exemplary anchor plate 40 and tattoo tool plate 42 respectively. Again, as with the previous embodiments, the plates 40 and 42 are simply one illustrated example of the attachment of the tattoo removal tool to the robotic arm, and it is to be understood that all other appropriate attachment mechanisms are within the scope of the present invention. The tattoo removal tool assembly 350 of FIG. 5 comprises a laser 358 with a tip 370. A laser controller 360 shown in phantom could be attached and included as part of the tattoo removal tool assembly 350, or it could be located remotely, or incorporated as part of the controller 114 of the robotic system illustrated in FIG. 1. The laser controller 360 may provide for selection and control of the level or radiation, energy density, pulse duration and frequency, beam size and shape.

In accordance with another aspect of the present invention, another new device and method for tattoo removal or neutralization is provided. Minute samples of tattoo pigment are retrieved for color and chemical analysis to optimize the removal program. Instead of removing the pigment, introduction of complementary pigment, for example, over the existing pigment produces a color consistent with the surrounding tissue to overwhelm or neutralize the existing tattoo, therefore, accomplishing the tattoo "removal." The video monitoring and analysis of the color spectrum may be very advantageous in this tattoo neutralization method, including precise color analysis and analysis of the chemical composition. Since the video image can be magnified significantly, it becomes feasible to retrieve individual pigment particles, rather than merely breaking them up; the video may see the pigment particles beneath the surface by adjusting the wave length of the video monitor so it maximizes the pigment image and minimizes the image of the normal tissue. With marked improvement over localizing of the individual pigment particles, micro-needle injection or pressure injection of bleaching of decolorizing agents can be used to neutralize the pigments. Since the array of agents that might be addressed is greater with robotic tattoo removal than with conventional tattoo removal, removal of traumatic pigmentation types of tattoo can be done, such as traumatic tattoos where a colored substance is introduced into the skin coincident with an accident, such as a deep abrasion from a dark colored roadway introducing dark particles to discolor the skin. The disclosure above related to system and methods for color matching is equally applicable here with an understanding that the placement of a new pigment or color in case of tattoo removal should correspond to the location of the pre-existing tattoo or other feature that is intended to be removed or neutralized, and that the color of the new pigment is chosen such that when placed over the color of the existing tattoo, their combined effect is to make the unwanted image disappear or match the normal skin color.

The basic method of the tattoo neutralization of the present invention using multiple injections of the complimentary or neutralizing pigments is described below. An image of the existing tattoo to be removed, preferably with the adjacent skin area, is obtained. It could be accomplished using any appropriate image acquisition devices, for example, one or more cameras, which in some embodiments may be mounted on the robotic arm. In one embodiment, the area of the unwanted tattoo is scanned. The colors of the obtained tattoo image to be neutralized are analyzed with the assistance, for example, of the processor of FIG. 1. The colors of each element or point of the tattoo to be neutralized may be analyzed chromatographically, or by any other known means. The analysis may be accomplished by each line or homogeneous field, or each pixel. Also, the color(s) of the adjacent skin area are analyzed as well so that "a normal" skin color in the relevant area of the body surface is determined. Embodiments of the method of the present invention further include a determination of what "complementary" or "neutralizing" color (when added to the existing tattoo color) would produce a color approximating the normal skin color. The application of the complementary color to the point of the tattoo to be removed is accomplished, for example, with the assistance of the robotic arm. Alternatively, the method of tattoo removal of the present invention may comprise analyzing the colors of the obtained image and the adjacent skin area and based on such analysis determine the best appropriate options for tattoo removal for the entire tattoo or for each region of the tattoo. For example, if the option chosen involves robotic laser tattoo removal, then the type of laser is also determined; alternatively an injection of the neutralizing or complementary color pigment to hide the tattoo may be chosen. The final plan for removing the entire tattoo may be chosen and it may involve any of the above methods in some combination for various parts or elements of the tattoo.

The forgoing illustrated and described embodiments of the invention are susceptible to various modifications and alternative forms, and it should be understood that the invention generally, as well as the specific embodiments described herein, are not limited to the particular forms or methods disclosed, and that many other embodiments are possible within the spirit and the scope of the present invention. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments. Thus, the illustrated and described embodiments are for purposes of better understanding, and not limitation, of the inventions disclosed herein.

What is claimed is:

1. A method for color matching at least one element of a new tattoo to a field on a body surface comprising:
   identifying in an image of a body surface to be tattooed a field to which a color of at least one element of a new tattoo is to be matched;
   processing the image to determine a color spectrum of the field; and
   color matching the at least one element of the new tattoo to one or more colors of the color spectrum of the field.

2. The method of claim 1, further comprising registering the image with a robotic system.

3. The method of claim 2, wherein registering the image with the robotic system is accomplished by means of at least one fiducial mark.

4. The method of claim 3, wherein at least a portion of a pre-existing tattoo is used as the at least one fiducial mark.

5. The method of claim 1, further comprising applying the color matched new tattoo on the body surface using a robotic system.

6. The method of claim 5, further comprising maneuvering a robotic arm to position a tattoo tool carried by the robotic arm proximate a location on the body surface where the new tattoo is intended to be created.

7. The method of claim 1, wherein the field is a pre-existing tattoo or a portion thereof.

8. The method of claim 1, wherein the field is a portion of a skin surface and a color of the at least one element of the new tattoo is chosen to compliment a color of the portion of the skin surface.

9. The method of claim 1, wherein the body surface comprises a tissue with a deficient or abnormal color, the field comprises a normal skin color, and color matching of the at least one element of the new tattoo to the field comprises adding one or more colors to the tissue with a deficient or abnormal color to simulate the normal skin color.

10. The method of claim 1, wherein the new tattoo is one or more of an extension, a modification, or an enhancement of a pre-existing tattoo.

11. The method of claim 1, wherein the field is adjacent a birth mark, scar tissue or tissue with absent, deficient or abnormal pigment.

12. The method of claim 1, further comprising identifying a new tattoo image to be matched, wherein identifying the tattoo image comprises selecting the tattoo image from a collection of one or more images, downloading a desired image from an external source, or creating a new desired tattoo image.

13. The method of claim 12, further comprising modifying the identified new tattoo image as desired or to fit the size and location of the body surface.

14. A system for color matching at least one element of a new tattoo to a field on a body surface, comprising:
   an image acquisition device; and
   an image processor, the image processor configured for:
      processing an image obtained by the image acquisition device, the obtained image including a field to which a color of at least one element of a new tattoo to be matched;
      analyzing a color spectrum of the field; and
      color matching the at least one element of the new tattoo to one or more colors of the color spectrum of the field.

15. The system of claim 14, wherein the image acquisition device is one or more cameras and the image processor is a computer.

16. The system of claim 14, wherein the image processor is further configured to analyze and choose colors based at least in part on a selected criteria.

17. The system of claim 14, further comprising:
   a robotic arm; and
   a tattoo tool carried by the robotic arm, the tattoo tool being operable using a substantially automated process to deliver a pigment for color matching.

18. The system of claim 14, further comprising a collection of tattoo images stored in the image processor.

19. The system of claim 14, further comprising a plurality of reservoirs, each reservoir containing a color pigment, and wherein a tattoo tool is adapted to be selectively coupled to a respective one or more of the plurality of reservoirs to control colors of the new tattoo.

20. The system of claim 14, further comprising a user interface that allows a system operator to input instructions relating to one or more of a type, location, orientation, size, configuration, depth or color of the new tattoo.

21. An image processor for color matching at least an element of a new tattoo to a field on a body surface, the image processor configured for:
   receiving an image of a body surface to be tattooed, the image including a field on the body surface to which a color of at least one element of a new tattoo is to be matched;
   processing the image to analyze a color spectrum of the field; and
   color matching the at least one element of the new tattoo to one or more colors of the color spectrum of the field.

* * * * *